(12) United States Patent
Moerman et al.

(10) Patent No.: US 6,706,159 B2
(45) Date of Patent: *Mar. 16, 2004

(54) COMBINED LANCET AND ELECTROCHEMICAL ANALYTE-TESTING APPARATUS

(75) Inventors: Piet H. C. Moerman, Lexington, MA (US); Jerome F. McAleer, Wantage (GB); Matthias Stiene, Inverness (GB)

(73) Assignee: Diabetes Diagnostics, Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/518,075

(22) Filed: Mar. 2, 2000

(65) Prior Publication Data

US 2002/0130042 A1 Sep. 19, 2002

(51) Int. Cl.$^7$ ............................................. G01N 27/327
(52) U.S. Cl. ........................... 204/403.03; 204/403.02; 600/584; 606/182; 606/184; 606/185
(58) Field of Search ............................. 204/403, 403.01, 204/403.02, 403.03, 403.04, 403.05; 600/584, 576, 583; 606/181, 182, 184, 185, 167

(56) References Cited

U.S. PATENT DOCUMENTS

| | | | |
|---|---|---|---|
| 4,203,446 A | 5/1980 | Hofert et al. |
| 4,462,405 A | 7/1984 | Ehrlich |
| 4,624,253 A | 11/1986 | Burns |
| 4,627,445 A | 12/1986 | Garcia et al. |
| 4,637,403 A | 1/1987 | Garcia et al. |
| 4,895,147 A | 1/1990 | Bodicky et al. |
| 4,924,879 A | 5/1990 | O'Brien |

(List continued on next page.)

FOREIGN PATENT DOCUMENTS

| | | |
|---|---|---|
| EP | 0 964 060 A2 | 12/1999 |
| JP | 4-194660 * | 4/1992 |
| WO | WO 97/19344 | 5/1997 |
| WO | WO 97/42882 | 11/1997 |
| WO | WO 98/24366 | 6/1998 |

*Primary Examiner*—Kaj K. Olsen

(57) ABSTRACT

An apparatus for detection and quantitation of an electrochemically-detectable analyte, such as glucose, in blood or interstitial fluid includes a meter unit, a lancet and an electrochemical sensor. Of these components, the meter is preferably reusable, while the lancet and the electrochemical sensor are preferably incorporated in assemblies intended for single-use. The meter unit has a housing, within which a lancet is engaged with a mechanism for moving then lancet; a connector disposed within the housing for engaging an electrochemical sensor specific for the analyte and transmitting a signal indicative of the amount of analyte, and a display operatively-associated with a connector for displaying the amount of the analyte to user. The electrochemical sensor is adapted for detection of a particular analyte. In addition, the electrochemical sensor has an absorptive member for uptake of a sample of blood or interstitial fluid. In one version, the lancet moves from a initial position to a piercing position in which skin of the user is pierced and optionally back to a retracted position. The electrochemical sensor is disposed such that the absorptive member takes up a sample from the pierced skin of the user when it is pierced by the lancet without movement of the apparatus. In an alternative version, the lancet is a hollow cannula through which blood or interstitial fluid is transported from the puncture site to an absorbent portion of the electrochemical sensor. In either version, the apparatus provides single-step operation in which sample acquisition and analysis occur as a result of the single action of pressing the apparatus against the users skin.

10 Claims, 14 Drawing Sheets

U.S. PATENT DOCUMENTS

| | | | |
|---|---|---|---|
| 5,201,324 A | | 4/1993 | Swierczek |
| 5,269,799 A | | 12/1993 | Daniel |
| 5,395,387 A | | 3/1995 | Burns |
| 5,395,504 A | * | 3/1995 | Saurer et al. ............... 204/403 |
| 5,458,140 A | * | 10/1995 | Eppstein et al. ............ 606/181 |
| 5,497,772 A | * | 3/1996 | Schulman et al. .......... 204/403 |
| 5,505,212 A | * | 4/1996 | Keljmann et al. .......... 606/181 |
| 5,540,709 A | | 7/1996 | Ramel |
| 5,582,184 A | | 12/1996 | Erickson et al. |
| 5,613,978 A | | 3/1997 | Harding |
| 5,680,872 A | | 10/1997 | Sesekura et al. |
| 5,682,233 A | | 10/1997 | Brinda |
| 5,730,753 A | | 3/1998 | Morita |
| 5,733,300 A | | 3/1998 | Pambianchi et al. |
| RE35,803 E | | 5/1998 | Lange et al. |
| 5,746,217 A | | 5/1998 | Erickson et al. |
| 5,797,940 A | | 8/1998 | Mawhirt et al. |
| 5,820,570 A | | 10/1998 | Erickson et al. |
| 5,823,973 A | | 10/1998 | Racchini et al. |
| 5,859,937 A | | 1/1999 | Nomura |
| 5,871,494 A | | 2/1999 | Simons et al. |
| 5,879,310 A | | 3/1999 | Sopp et al. |
| 5,879,367 A | | 3/1999 | Latterell et al. |
| 5,891,053 A | | 4/1999 | Sesekura |
| 5,916,230 A | | 6/1999 | Brenneman et al. |
| 5,938,679 A | | 8/1999 | Freeman et al. |
| 5,951,493 A | | 9/1999 | Douglas et al. |
| 5,984,940 A | | 11/1999 | Davis et al. |
| 6,022,366 A | | 2/2000 | Schraga |
| 6,027,459 A | | 2/2000 | Shain et al. |
| 6,063,039 A | | 5/2000 | Cunningham et al. |
| 6,066,103 A | | 5/2000 | Duchon et al. |
| 6,071,250 A | | 6/2000 | Douglas et al. |
| 6,143,164 A | * | 11/2000 | Heller et al. .............. 205/777.5 |
| 2002/0198444 A1 | | 12/2002 | Uchigaki et al. |

* cited by examiner

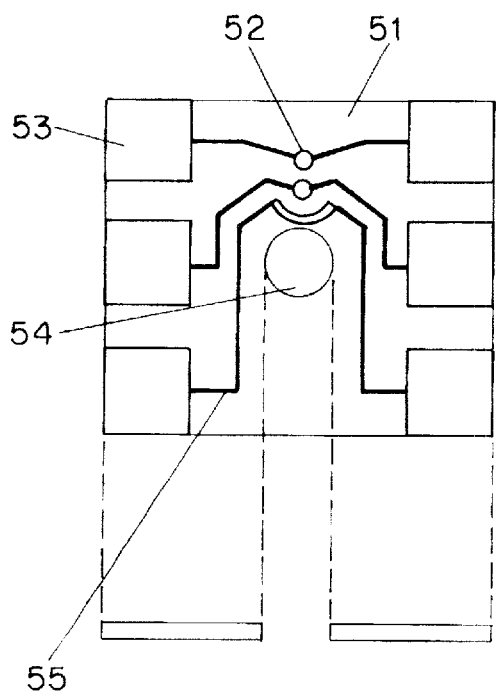
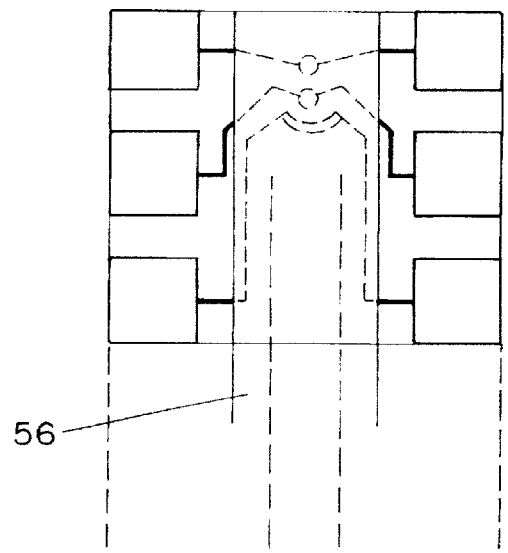
FIG. 5A       FIG. 5B
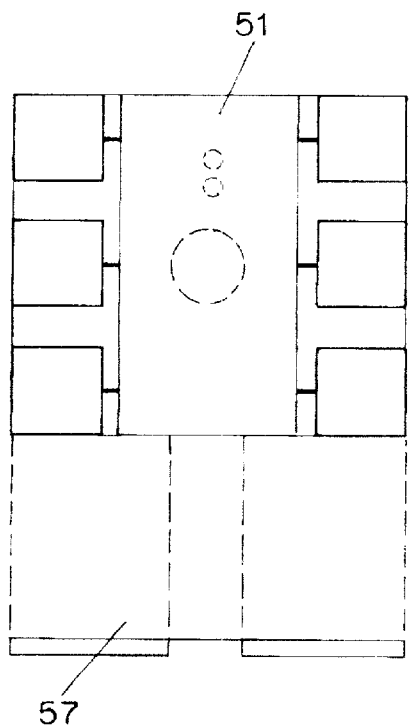
FIG. 5C

COMBINED LANCET AND ELECTROCHEMICAL ANALYTE-TESTING APPARATUS

FIELD OF THE INVENTION

This application relates to an electrochemical apparatus for the detection of analytes, and particularly glucose, in blood or interstitial fluid.

BACKGROUND OF THE INVENTION

Glucose monitoring is a fact of everyday life for diabetic individuals, and the accuracy of such monitoring can literally mean the difference between life and death. To accommodate a normal life style to the need for frequent monitoring of glucose levels, a number of glucose meters are now available which permit the individual to test the glucose level in a small amount of blood. Many of these meters detect glucose in a blood sample electrochemically, by detecting the oxidation of blood glucose using an enzyme such as glucose oxidase provided as part of a disposable, single-use electrode system. Examples of devices of this type are disclosed in European Patent No. 0 127 958, and U.S. Pat. Nos. 5,141,868, 5,286,362, 5,288,636, and 5,437,999 which are incorporated herein by reference.

To use these meters, the user pricks a finger or other body part to produce a small sample of blood or interstitial fluid which is then transferred to the disposable electrode system. This can cause problems, because of the need to take several measurements a day. The biggest drawback to routinely drawing small blood samples is the pain inflicted by the currently available lancets or finger-sticking devices. The most favored site of sampling is the rich capillary bed of the skin of the finger tip which readily yields a drop of blood from a small cut. The finger tip is also rich in pain receptors, and the pain is increased when the incision is too deep, or is too close to a recent incision, or is not deep enough requiring an additional incision. The pain maybe also be increased if the cutting blade penetrates slowly or is withdrawn slowly. Furthermore, the user may be forced to make a larger incision than is necessary in order to get a drop of blood to form for transfer to the measuring strip. Because of this, different designs for lancing devices have been proposed which are designed to facilitate use of the device and limit the pain associated with the procedure. Examples of lancing devices are described in U.S. Pat. Nos. 4,924,879, 5,201, 324, 5,318,584, 5,879,311, and 5,879,367 which are incorporated herein by reference.

International Patent Publication No. WO95/10223 describes a device for collection of interstitial fluid. The device can include a membrane on which sample is collected and dried. This membrane is then transferred to an external device for analysis.

Each of these known devices for the electrochemical monitoring of glucose by a diabetic involves a two-step process, in which the skin is first pierced to obtain a sample and this sample is transferred to a sensor for analysis. This presents several drawbacks. First, the user must transfer blood into the detection apparatus which requires a measure of dexterity to align the drop of blood on the finger with the sample-receiving opening of the sensor or meter. Second, because of this transfer, the amount of blood or fluid extracted from the patient may be inappropriate for the sensor, either being too little to provide an accurate measurement or too much, which can increase the amount of pain associated with the procedure.

U.S. Pat. No. 4,637,403 discloses a self-contained device for lancing and testing blood glucose using colorimetry. U.S. Pat. No. 5,054,499 discloses a colorimetric device in which a lancet punctures an absorbent member which includes reagents for the colorimetric detection of glucose prior to puncturing the skin. U.S. Pat. Nos. 5,682,233 and 5,823,973 disclose a sampling device which is sized to allow it to be mated with a testing apparatus for optical analysis of a sample. U.S. Pat. No. 5,746,217 discloses a lancet in which a capillary tube is used to capture sample, which is there analyzed by infrared spectroscopy in the capillary. U.S. Pat. No. 5,879,310 discloses a device in which a lancet punctures the skin and the sample resulting sample of body fluid is transported for analysis in an optical system.

U.S. Pat. No. 4,953,552 discloses a device for electrochemical glucose detection in which reagents for generating the electrochemical signal are coated directly onto the lancet, and thus come into contact with the sample without further user intervention. In this device, there is no spring action to drive the needle, and the needle is simply pressed in by the user. This makes control of the puncture difficult. Furthermore, replacement of the lancet and reagent are inconvenient in the device as disclosed, and mass production of sensors would be difficult.

Thus, there remains room for improvement in the manner in which fluid samples are collected and analyzed.

SUMMARY OF THE INVENTION

The present invention provides an improved apparatus for detection and quantitation of an electrochemically-detectable analyte, such as glucose, in blood or interstitial fluid. The apparatus comprises a meter unit, a lancet and an electrochemical sensor. Of these components, the meter is preferably reusable, while the lancet and the electrochemical sensor are preferably intended for single-use.

The meter unit comprises a housing, means disposed within the housing for engaging a lancet and moving an engaged lancet, a connector disposed within the housing for engaging an electrochemical sensor specific for the analyte and transmitting a signal indicative of the amount of analyte, and a display operatively-associated with a connector for displaying the amount of the analyte to user. The electrochemical sensor is adapted for detection of a particular analyte. In addition, the electrochemical sensor comprises an absorptive member for uptake of a sample of blood or interstitial fluid. In one embodiment of the invention, when a lancet is engaged in the apparatus, the means for engaging and moving the lancet moves the lancet from a initial position to a piercing position in which skin of the user is pierced and optionally back to a retracted position, which may be the same as or different from the initial position. The electrochemical sensor is disposed such that the absorptive member takes up a sample from the pierced skin of the user when it is pierced by the lancet without movement of the apparatus. In an alternative embodiment, the lancet is a hollow cannula through which blood or interstitial fluid is transported from the puncture site to an absorbent portion of the electrochemical sensor. Thus, in either embodiment, the invention provides an apparatus with single-step operation in which sample acquisition and analysis occur as a result of the single action of pressing the apparatus against the users skin.

Another aspect of the invention relates to disposable sensor assemblies for use in a meter in accordance with the invention. Such disposable sensor assemblies may contain just the sensor in a support suitable for attachment to the meter or both the sensor and the lancet. In the latter case, the disposable sensor assembly may contain one sensor and one or more lancets, or it may contain a plurality of lancet/sensor pairs.

BRIEF DESCRIPTION OF THE DRAWINGS

FIGS. 5A–C show a specific embodiment of a sensor 32 for incorporation in a sensor assembly in accordance with the invention;

DETAILED DESCRIPTION OF THE INVENTION

The apparatus of the present invention is an integrated lancing and analysis device which does not require a separate action for the transfer of the sample from the puncture site to a strip for analysis. This apparatus includes a meter unit, in which the electronics for analysis of a sample and display of a result are located, a cutting member (i.e, a lancet or hollow needle) and an electrochemical sensor. The electrochemical sensor includes an "absorptive member" for the uptake of sample. As used in the specification and claims hereof, the term "absorptive member" encompasses various methods for achieving the direct transfer of a liquid sample from the sampling site to the electrochemical sensor, including but not limited to absorptive materials which take up liquid and cannula's through which liquid is transferred. The uptake of liquid may be a result of inherent capillarity resulting from the structure of the absorptive material or the size of the analysis chamber or cannula, or it may be an active absorption stimulated by application of suction.

Figure 1:
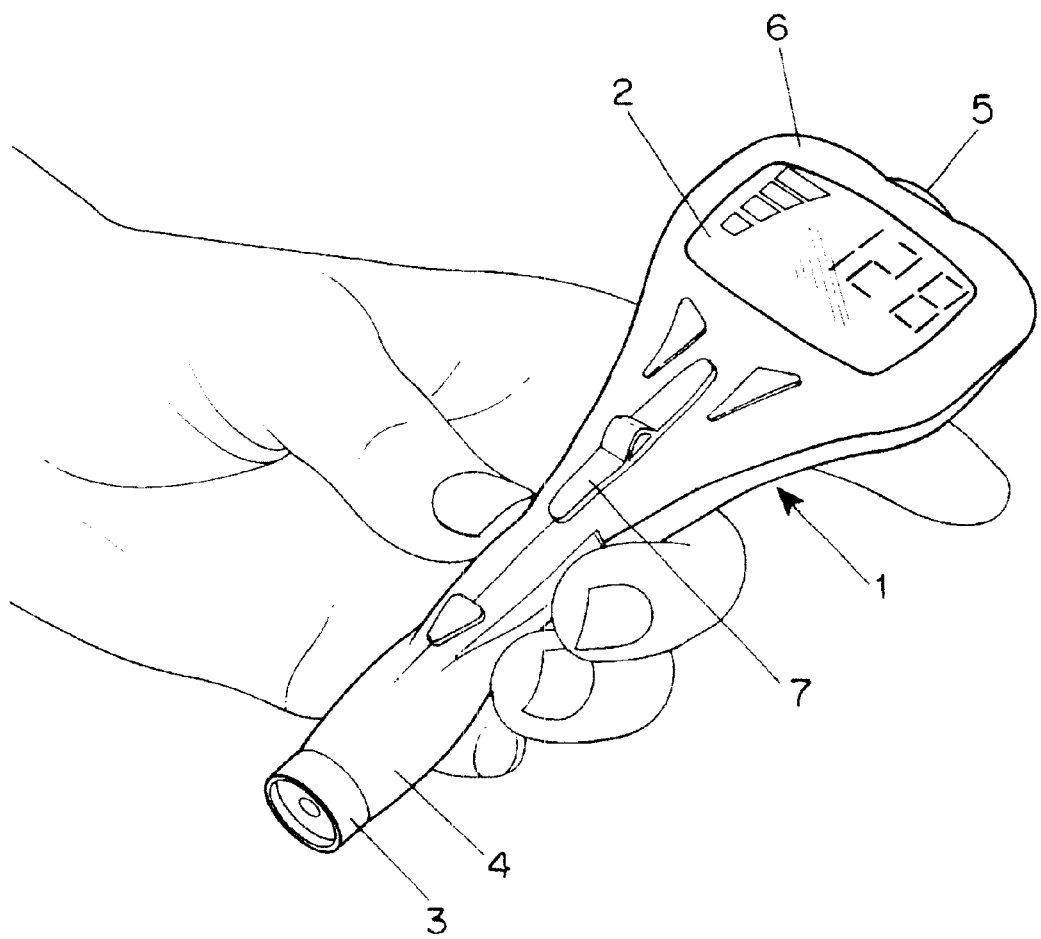
FIG. 1 shows an exterior view of an apparatus in accordance with the invention.

FIG. 1 shows an exterior view of an embodiment of an apparatus in accordance with the invention, although it will be appreciated that the overall shape of the device is a matter of design choice and is thus provided here solely for purposes of illustration. The device as shown allows for an easy grip by one hand, while providing good visibility of the display. In addition, it is easy to handle when sampling from alternative sites like the palm of the hand, the arm or the abdomen.

As shown, the device comprises a housing 1 of a size easily held in one hand. A display 2 is visible to the user on the outside of the housing 1. A skin-contact ring 3 is disposed at the sample end 4 of the device, while a button 8 for activating a sample/measurement cycle is disposed at the opposite end 6. Ejector slide 7 ejects used lancets and electrochemical sensors when it is shifted towards the sample end 4, and is also used to lock the device. Optional button 5 is used to set the penetration depth of the lancet.

Figure 2C:
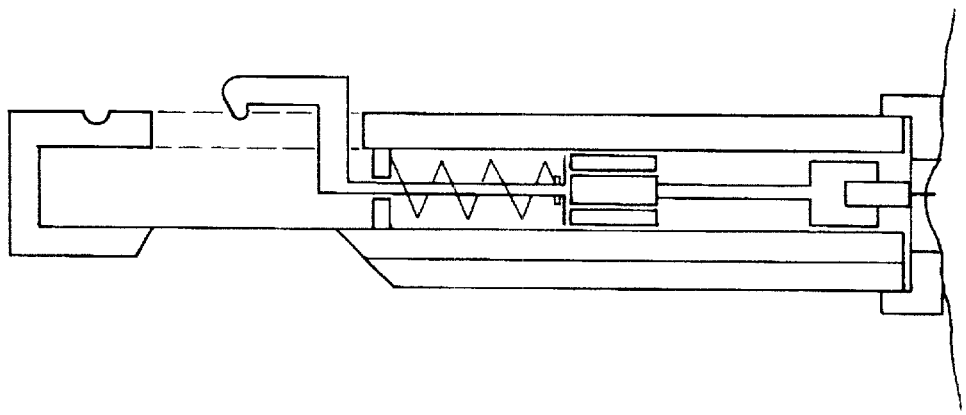
FIGS. 2A–C show sectional views of a device in accordance with the invention.
Figure 2B:
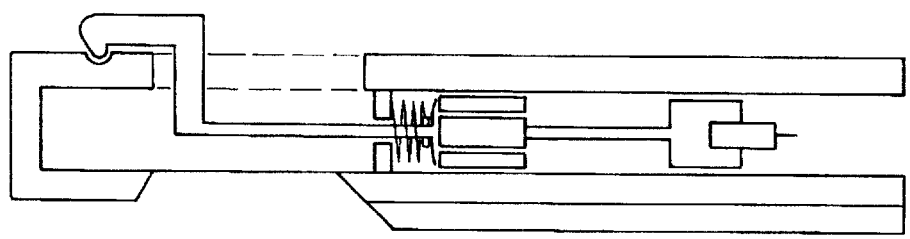
Figure 2A:
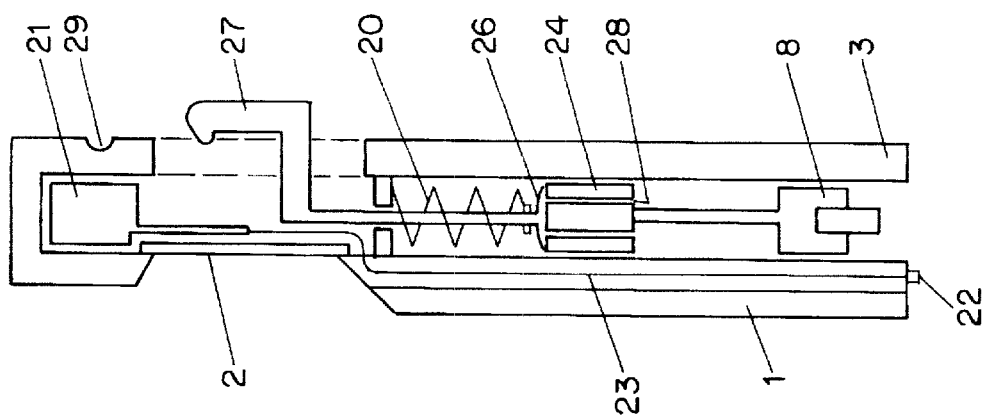

FIGS. 2A–C show sectional views of the device of FIG. 1 showing the internal mechanism for engaging and moving the lancet 20, the electronics 21 for transfer of an electrical signal from a sensor (not shown in FIG. 2) to the display 2. An electrical contact 22 is provided near the end of the housing 1 for making electrical contact with a sensor, and is connected to the electronics via a conductive element 23. The three figures illustrate the operation of the device.

In FIG. 2A, the device is shown in a rest position, prior to sampling. There is no tension on the spring 20. Plunger 24 is attached to the lancet holder 8 and to cocking button 27. The spring is attached to the lancet and bears on the lancet to allow both pushing out on the lancet from the cocked position and retraction of the lancet from a piercing position. Pores 28 allow air to move out of the space defined by a valve 26 and skin pressed against the skin-contact ring 3. The valve is a one-way valve which permits the flow of air from this space, but not into it. Catch 29 holds the cocking button 27 in place until released manually. To cock the device the cocking button 27 is pushed up to the catch 29, causing the lancet assembly and the valve to move upwards, compressing spring 20 as shown in FIG. 2B. The cocked device is then pressed against the skin and catch 29 is released. This results in the lancet assembly being driven downwards to puncture the skin as shown in FIG. 2C. During this downwards movement, pressure does not increase in the region between the plunger 24 and the skin because of the one-way valve 26. However, because the spring passes through its equilibrium position, there is a backwards motion of the lancet assembly after the skin is pierced and this motion results in the creation of reduced pressure in this region.

Figure 3A:
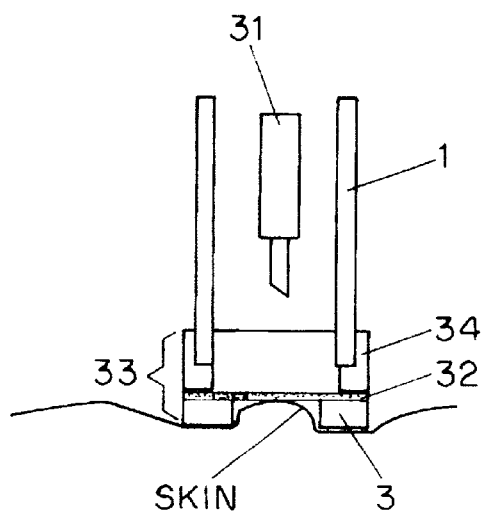
FIGS. 3A–C show a schematic representation of an arrangement of the sensor and the lancet in accordance with one embodiment of the invention.
Figure 3B:
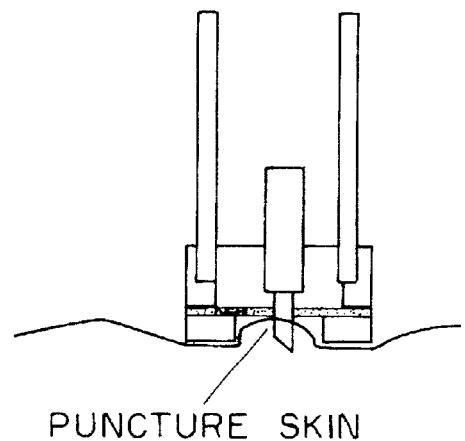
Figure 3C:
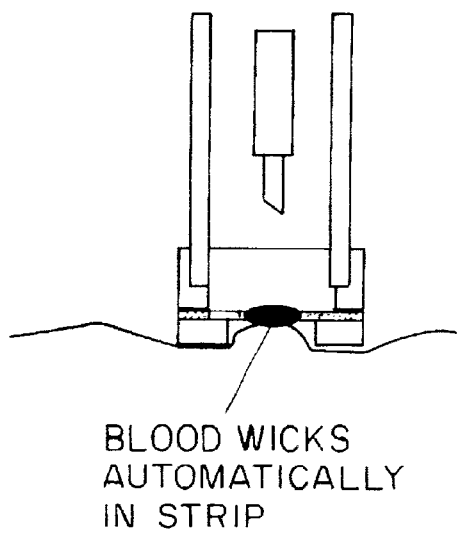

An important feature of the device of the present invention which enables true one-step operation is use of an arrangement of the lancet and sensor to allow "in situ" sampling without movement of the apparatus. FIGS. 3A–C show a schematic representation of one such arrangement. FIG. 3A shows the device in a ready-to-use state. The lancet 31 is disposed within the housing 1 and is engaged with the means for moving the lancet (not shown). The sensor strip 32 is part of a sensor assembly 33 that includes the skin-contact ring 3 and a collar 34 for coupling the assembly to the housing 1. The skin-contact ring 3 is pressed against the skin of the user, which causes an upwelling of tissue in the region surrounded by the skin-contact ring. When the device is activated, the lancet device 31 moves downward, piercing first the sensor 32 and then the skin as shown in FIG. 3B. The lancet 31 is then retracted, and blood or fluid flowing from the pierced skin wicks into the sensor. (FIG. 3C).

Figure 4:
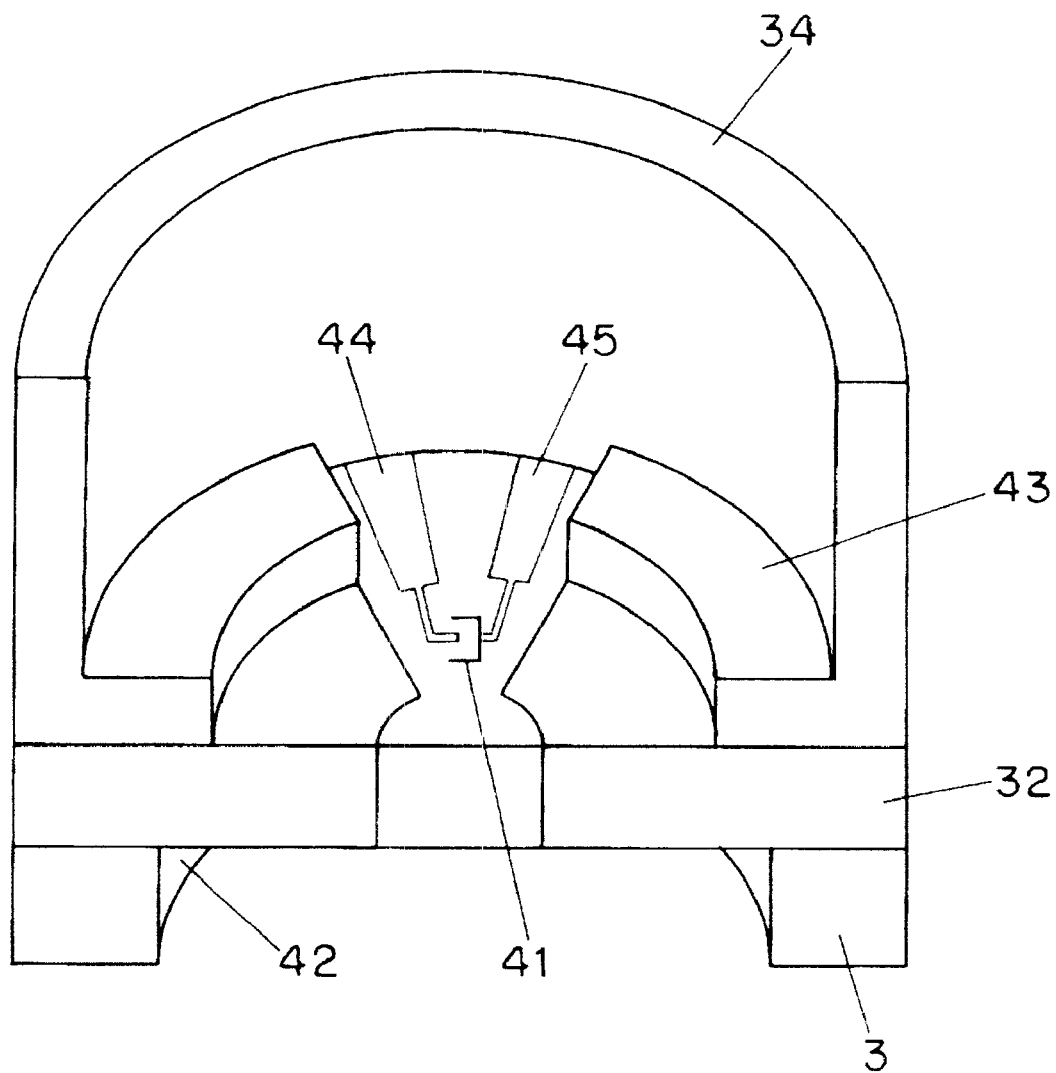
FIG. 4 shows an exemplary sensor assembly for electrochemical detection of an analyte.

In the embodiment of the invention as shown in FIGS. 3A–3C, the lancet 31 and the sensor assembly 33 are separate. The lancet used in this embodiment may be of conventional design compatible with the means for moving the lancet and the size of the housing. Various forms of lancets and associated means for moving the lancet are known in the art, including for example in U.S. Pat. Nos. 4,924,879; 5,196,025; 5,304,193 and 5,318,583, which are incorporated herein by reference. The sensor assembly is a novel component adapted for use in the present invention, and itself forms an aspect of the invention. FIG. 4 shows a cross section in greater detail of an exemplary sensor assembly for electrochemical detection of an analyte. As shown, the sensor 32 has a reagent pad 41 disposed in approximate alignment with one edge of the opening 42 defined by the skin-contact ring 3. The collar 34 has a lip 43 against which the housing 1 of the meter bears when the sensor assembly is attached to the meter. Electrical contacts 44 and 45 are accessible through an opening in the lip 43. An insulating pad may be provided so that conductivity between the connectors only occurs in the vicinity of the reagent pad when a liquid sample is present. When the housing 1 of the meter is inserted in the sensor assembly, electrical contact is made via electrical contacts 44 and 45.

In the sensor assembly of FIG. 4, the sensor 32 is disposed adjacent to the skin-contact ring 3 and extends across one end of the open space 42 defined with the skin-contact ring. The sensor comprises reagents 41 and electrodes for generation of an electrochemical signal in response to the presence of analyte and an adsorptive member for absorbing fluid placed within the central opening of the ring and transporting the fluid into reactive proximity to the reagents, and an electrical contact for transmitting the electrochemical signal from the sensor. The reagents are selected to provide an electrochemical signal in response to the presence of analyte. In the case of glucose, suitable reagents would include an enzyme capable of oxidizing glucose (for example glucose oxidase), and a mediator compound which transfers electrons from the enzyme to the electrode resulting in a measurable current when glucose is present. Representative mediator compounds include ferricyanide, metallocene compounds such as ferrocene, quinones, phenazinium salts, redox indicator DCPIP, and imidazole-substituted osmium compounds. Working electrodes have been formulated using materials of this type in a number of ways. For example, mixtures of conductive carbon, glucose oxidase and a mediator have been formulated into a paste or ink and applied to a substrate. See, EP 0 127 958 and U.S. Pat. No. 5,286,362 which are incorporated herein by reference.

FIGS. 5A–C show the assembly of a specific embodiment of a sensor 32 for incorporation in a sensor assembly in accordance with the invention. Contacts 53 and leads 55 are formed on a non-conductive substrate 51. In the embodiment shown in FIG. 5A, three set of contacts and three sets of leads are formed to create two working electrodes with reagents 52 and one reference electrode. The contacts and leads are suitably formed from conductive carbon inks, although other conductive materials may also be used. The electrodes may be formed by printing. Groups of sensors are suitably formed on a sheet of material and then cut apart for use.

The substrate 51 may advantageously be formed from a material which is sufficiently strong that the lancet will not pierce through the substrate material. This avoids contamination issues in the event of faulty lancet alignment. In this case, however, the substrate 51 needs to have an opening 54 or a weak spot through which the lancet can pass. Suitable materials for the substrate include polyester strips, high density polyethylene and ABS.

After the electrodes have been formed, a wick layer 56 is placed over the opening 54 and the electrodes, including the reagent pads 52 (FIG. 5B). This wick acts as an absorbent member to draw sample into the sensor and guide it to the electrodes. Suitable materials include nylon mesh. In some cases, however, no separate wick is necessary, as when the hole 54 in the substrate 51 inherently provides a capillary channel to the reagent pads 52 of the electrodes. Polymer film layers could also be used instead of or in combination with a wick to define a capillary channel for absorption of the sample to the electrodes.

Over the wick (if present) and the electrodes a print of an insulation ink 57 is provided. The insulation ink holds the wick in place, and defines the path through which sample can migrate. Thus, the insulation ink includes an opening having a hole 571 in alignment with the hole 54 and a contiguous region 572 extending over the reagent pads 52 of the electrodes. Contacts 53 remain exposed outside the edges of the insulating ink print 57 for making contact with the meter. Optionally, a top cover can be added to protect the reactants. Such a top cover could be made form a polymeric film such as polyester.

Figure 5D:
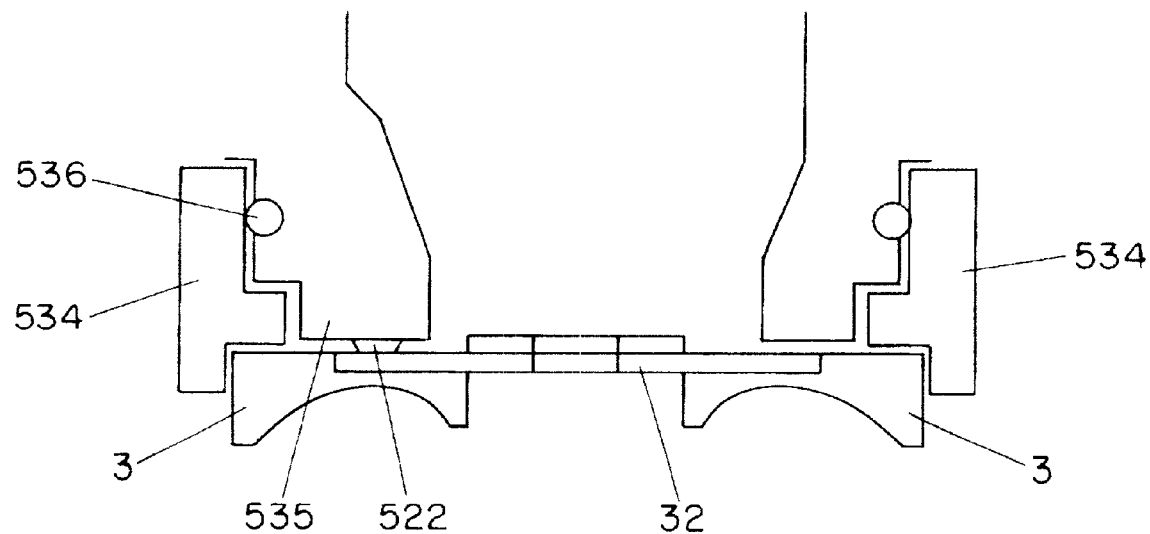
FIG. 5D shows an further embodiment of a sensor assembly in accordance with the invention.

The sensor of FIGS. 5A–C may be assembled with a skin contact ring and collar as shown in the FIG. 4. FIG. 5D shows an alternative configuration. Sensor 32 is supported on a skin contact ring 3. A collar 534 is affixed to the edge of the skin contact ring 3 and sized to receive the distal end 535 of the meter unit. O-rings 536 provide a tight seal between the collar 534 and the distal end of the meter unit 535. A contact 522 on the distal end of the meter unit 535 makes electrical contact directly with the contact portions of the sensor (for example contacts 53 in FIG. 5A).

Figure 6A:
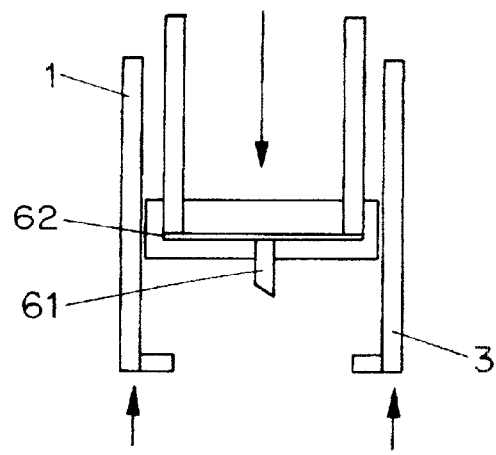
FIGS. 6A–C show an schematic representation of an alternative embodiment of the invention.
Figure 6B:
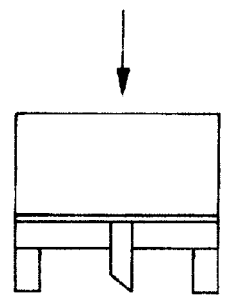

FIGS. 6A and 6B show a schematic representation of an alternative embodiment of the invention. In this case, the lancet 61 is a hollow cannula disposed adjacent to the sensor 62. The lancet 61 and the sensor 62 can be fabricated as a single unit which is loaded into a housing 1 for use. The housing desirably includes a skin-contact ring 3 which creates pressure to displace blood or interstitial fluid out of a puncture created by the lancet 61. When the device is activated, the lancet and the sensor are driven downwards as a unit to puncture the skin. (FIG. 6B) The sample is then drawn up through the lancet to the sensor. The dwell time in the piercing position is long enough to permit sufficient sample to be drawn into the sensor. Alternatively, the movement of the lancet may be in only one direction, with the entire device being moved away when sufficient sample has been collected. As discussed in more detail below, this latter option can be facilitated by the use of a device which provides an audible or other signal to the user when sufficient sample has been collected.

Figure 6C:
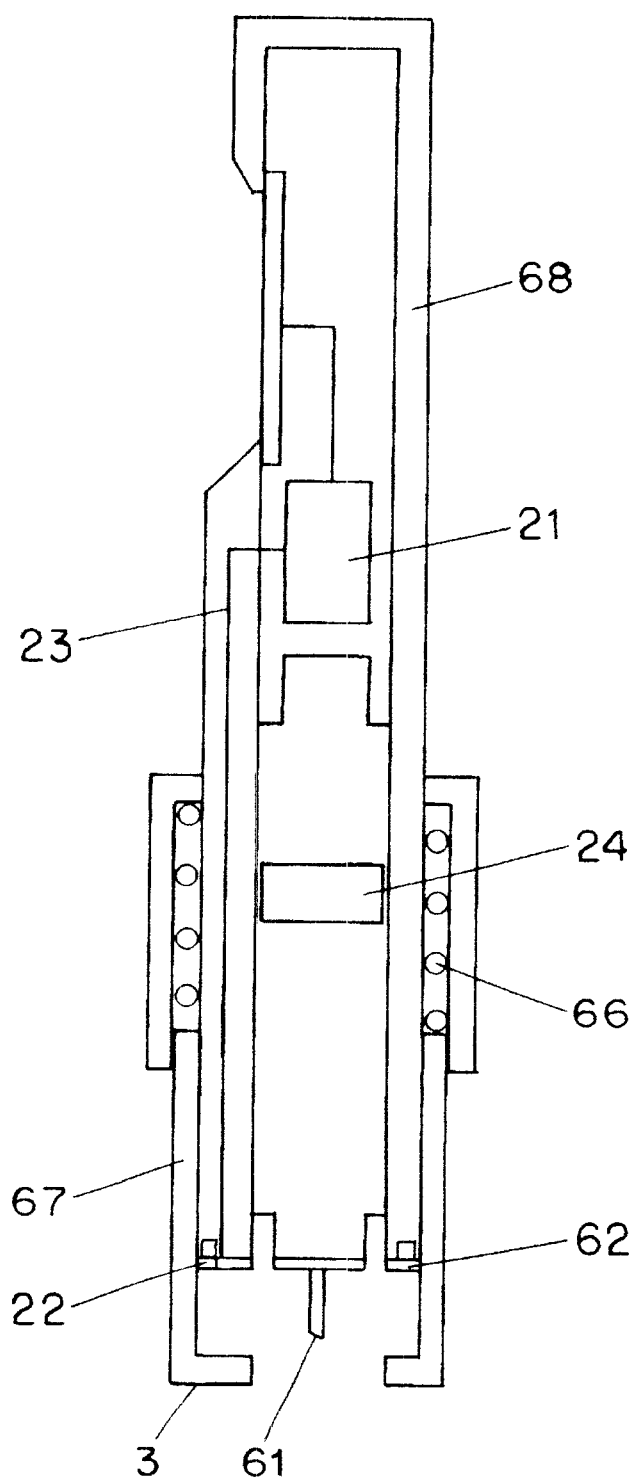

FIG. 6C shows an apparatus in accordance with the invention including a sensor assembly of the type shown in FIGS. 6A and 6B. In this apparatus, the sensor 62 has an integral lancet 61, and is slidably received in a first housing portion 67. The distal end 3 of the first housing portion 67 is pressed against the skin of the user, causing the compression of spring 66 and the exposure of the lancet for piercing of the users skin. When the apparatus is removed from the skin, the spring 66 causes the first housing portion 67 to move outward, to once again shield the end of the lancet. The sensor 66 is in electrical contact with a contact 22 which in turn is in electrical contact with the electronics 21 via a connector 23. A vacuum plunger 24 is disposed within a second part of the housing 68 for creating a suction to draw in blood or fluid.

Figure 7:
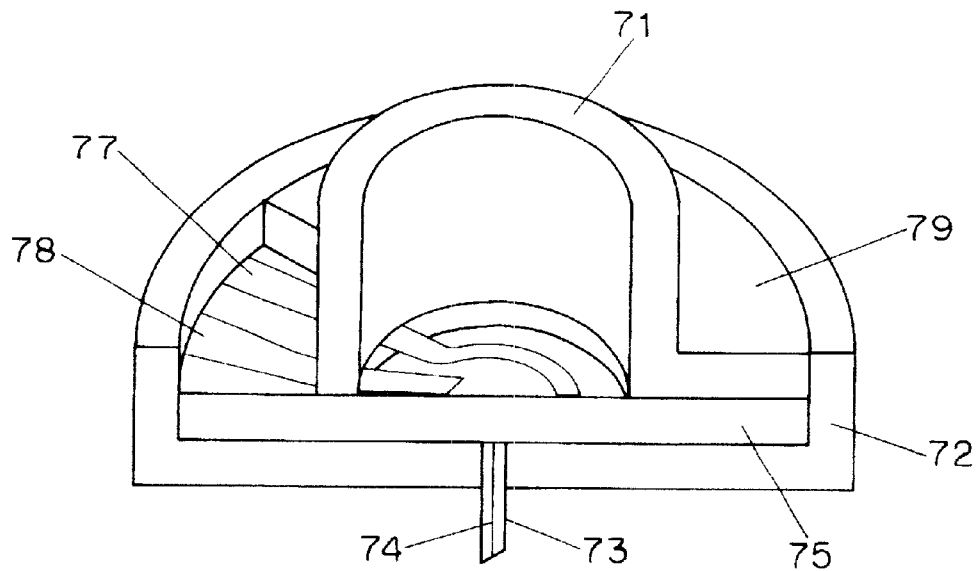
FIG. 7 shows a cross-section of an embodiment of a sensor assembly for use in the embodiment of the invention shown in FIG. 6.

FIG. 7 shows a cross-section of an embodiment of a sensor assembly for use in the embodiment of the invention shown in FIG. 6. The assembly includes a collar portion 71 and a base portion 72. These portions can be made as a continuous piece of material or they may be made from separate pieces joined together, for example with an adhesive. A hollow lancet 73 passes through the base portion 72, such that the hollow interior 74 of the lancet is in contact with the sensor 75. The sensor may extend over a greater area than the collar portion, as shown, or a lip extending from the interior surface of the collar may be utilized to hold the sensor 75 in place. The second portion of the housing 68 may bear on this lip, or in the embodiment shown in FIG. 7 on an annular surface 79 surrounding the collar 71. Electrical contact is made through an opening in this annular surface 79, for example via contacts 77, 78. Contacts 77, 78 may also be formed on the interior wall of the collar portion. The sensor 75 may have the same type of structure as shown in FIG. 5. Reagents may also be disposed directly on the lancet, or in a lancet lumen.

FIGS. 8A–G shows a further embodiment of the invention. The device can operate manually (no automatic timing function) or perform a test procedure on demand from the meter. In the latter case, the meter housing 81 contains a plurality of lancet/sensor pairs and a timing mechanism for automatically using the pairs at pre-defined time intervals. The length of the pre-defined time interval is related to the number of lancet/sensor pairs and to the frequency with which testing for the target analyte is desired. For example, in a device for testing for blood glucose, with twelve lancet/sensor pairs, the time interval is suitably between one and four hours. This results in a need to replace the lancet/sensors at reasonable intervals, for example twice a day, once a day, or once every other day. The timing can also be shorter, for example every minute, or can be selected using a logic circuit. Thus, for example, in the case of a rapidly changing glucose level (as determined by the difference between two successive measurements), the logic circuit in the meter may be configured to decrease the interval between subsequent measurements until such time as the glucose level stabilizes. The meter may also be configured to take several initial readings at short time intervals to determine a suitable baseline test interval based on the degree of variations in the results. This baseline test interval may be used for all subsequent measurements in the test cycle, or it may be shortened as described above in response to changes in glucose levels.

Figure 8A:
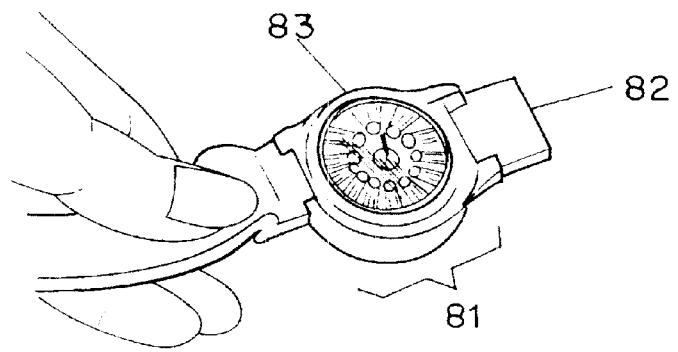
FIGS. 8A–G show a further embodiment of the invention.
Figure 8B:
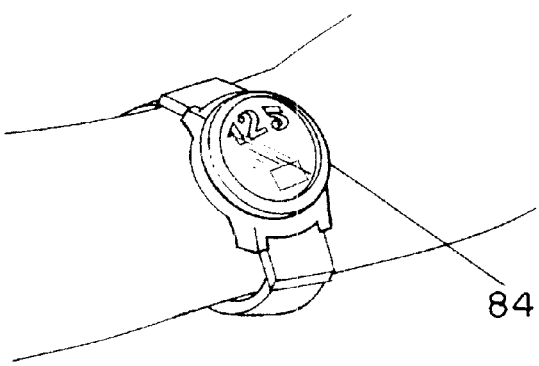
Figure 8C:
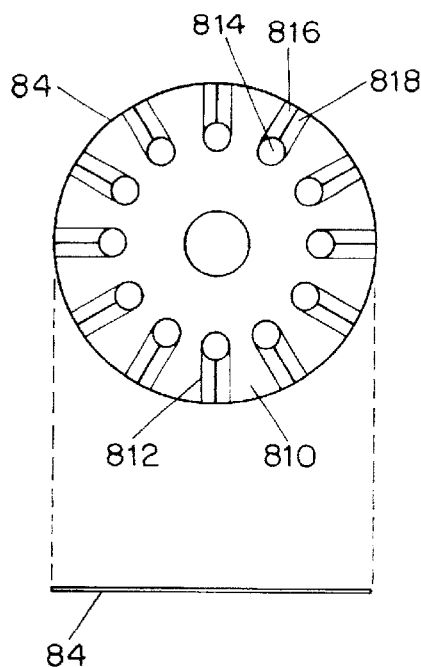

A suitable format for an embodiment of the invention in which the housing contains a plurality of lancet/sensor pairs is the watch-type format as shown in FIGS. 8A and 8B. The apparatus comprises the housing 81 and a strap 82. The housing has a bottom side 83, through which contact is made between the lancets and the skin of the user (shown in FIG. 8A), and a top side 841 (shown in FIG. 8B) on which the test results are displayed. The device may be strapped like a watch around the wrist of a user, as shown in FIG. 8B, or about the forearm or upper arm. Once in place, the device is activated and a number of tests may be automatically performed without further action by the user and the result are displayed, individually or as a summary of a number of tests on the display. Alternatively, the device or the sensor disk may be self-attaching (for example using a skin-compatible adhesive). This provides utility on any body surface, and eliminates the need for a strap.

FIGS. 8C–F show an exploded view of the component parts of an apparatus in accordance with this embodiment of the invention. Closest to the bottom side 83 of the apparatus is a sensor disk 84. The sensor disk 84 comprises a substrate 810 on which are formed a plurality of sensors 812. Each sensor includes a reagent pad 814 in contact with a pair of electrodes 816, 818. The sensor disk 84 has a central opening to allow the trigger mechanism (the spindle/ramp) to pass through. The sensor as a whole is bonded together with glue, ultrasonic welding or with snap-together fittings.

Figure 8D:
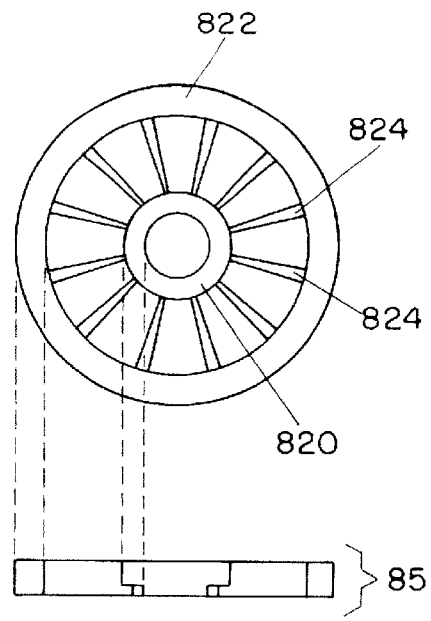

Above and coaxial with the sensor disk 84 is placed a spacer ring 85 (FIG. 8D). The spacer ring 85 provides a defined area surrounding each sensor 812, so that fluids contacting one sensor will not interact with adjacent sensors. Alternatively, the insulation print or capillary channels can provide this isolation. As shown, sensor ring 85 has a hub 820, a rim 822 and a plurality of spokes 824. The separator ring 85 is placed over the sensor disk 84 such that one sensor 812 is positioned in the space between each adjacent pair of spokes 824. The rim may include electrical contacts for conducting signal indicative of the amount of analyte from the electrodes 816, 818 of each sensor pair.

Figure 8E:
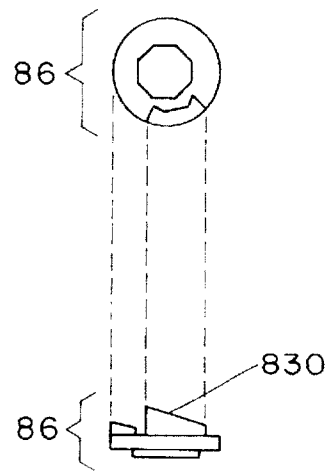
Figure 8F:
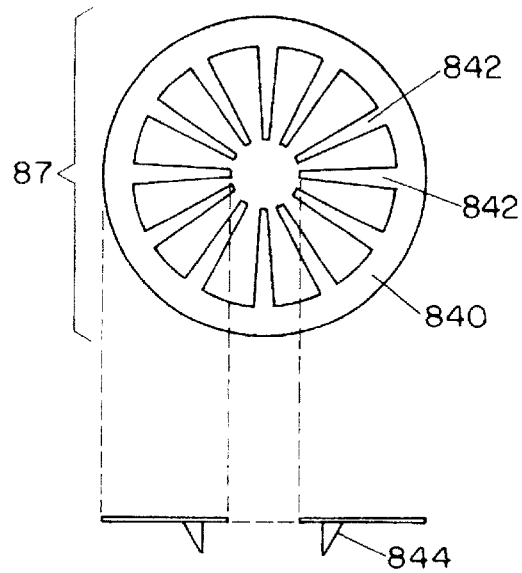

Over and coaxial with the separator ring 85 is placed a cam ring 86 (FIG. 8E). The cam ring has a ramp portion 830, such that rotation of the cam ring 85 results in an increase in the thickness of the cam ring 86 when viewed at a fixed location. The cam ring 86 has a central opening through which a screw or similar fastener is inserted to assemble the completed device. The opening preferably has a faceted or toothed edge, however, to allow engagement of the cam ring 86 with a drive mechanism for rotating the cam ring.

Over and coaxial with the cam ring 86 is a lancet ring 87. The lancet ring 87 has a rim 840 and a plurality of lancet spokes 842, each of which has a free center end. The lancet ring 87 is positioned such that each lancet spoke 842 is aligned with a space between the spokes 824 of the separator ring 85. The lancet spokes 842 are made of a flexible material with substantial memory such as spring steel. A lancet 844 is attached to each lancet spoke 842 near the center-end of the lancet spoke 842, oriented in a downward direction so that the point of the lancet 844 is directed towards the sensor disk 84. The lancet spokes 842 are of a length such that they interact with the cam ring 86 lying beneath the lancet spokes. When the device is first assembled, one of the lancet spokes (arbitrarily referred to as the first lancet spoke) is substantially aligned with highest part of the ramp portion 830 and is thus deflected upwards from its neutral or rest position. When the cam ring 86 is rotated a partial turn, this first lancet spoke is moved off the end of the ramp and springs downward, piercing through the underlying sensor disk 84 and the skin of the user. At the same time, the "second" lancet spoke is moved into position at the highest part of the ramp portion 830, and each of the other lancet spokes is shifted to a position of increased deflection. Thus, each partial rotation of the cam ring 86 brings about one sampling and measurement activity.

Figure 8G:
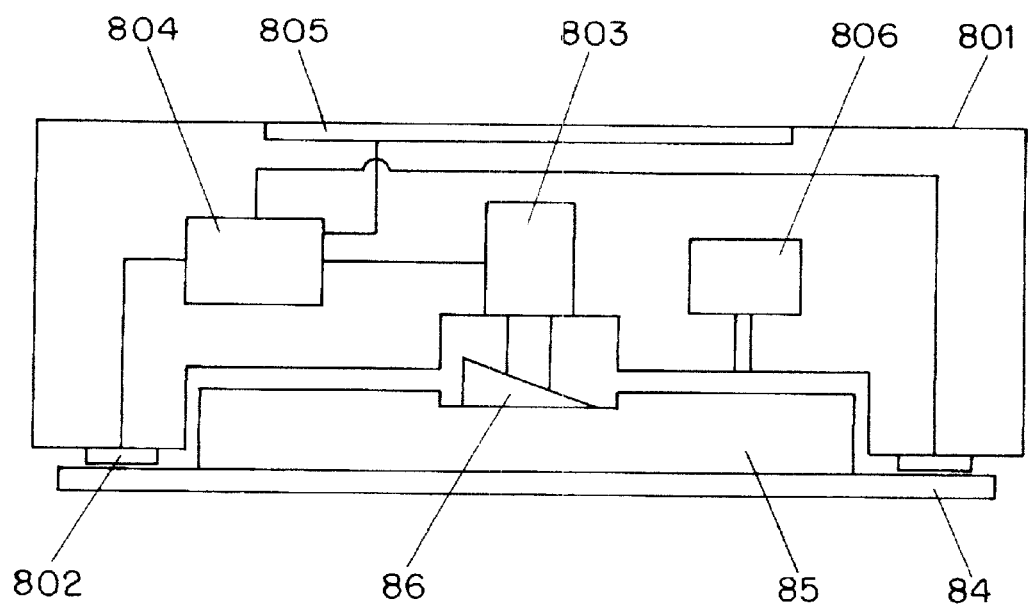

FIG. 8G shows a cross section of an assembled device incorporating a sensor system assembly of the type shown in FIGS. 8A–F. Spacer ring 85 is received within an opening on the bottom of a housing 801. Sensor disk 84 is disposed exterior to the housing, and has a larger diameter than the spacer ring 85 such that it can make electrical contact with contacts 802 disposed on the bottom of the housing. A small motor 803, such as a stepper motor, is engaged with the cam ring 86 to rotate it with respect to the sensor assembly, thereby sequentially activating the lancets associated with the sensors. The motor 803 is controlled by electronics 804, which also receive signal from the contacts 802, process the signal and transmit instructions for an appropriate display to the display 805. A small vacuum pump 806 (for example a membrane pump or actuator pump) is also disposed within the housing 801 to create a suction which draws sample into the sensors. This pump may be on continuously, or it may be controlled by the electronics to be active for a period of time spanning the activation of the motor to rotate the cam ring. Alternatively, the vacuum pump could be activated prior to lancing, with a sufficient underpressure acting as a signal to start the lancing cycle.

Figure 9A:
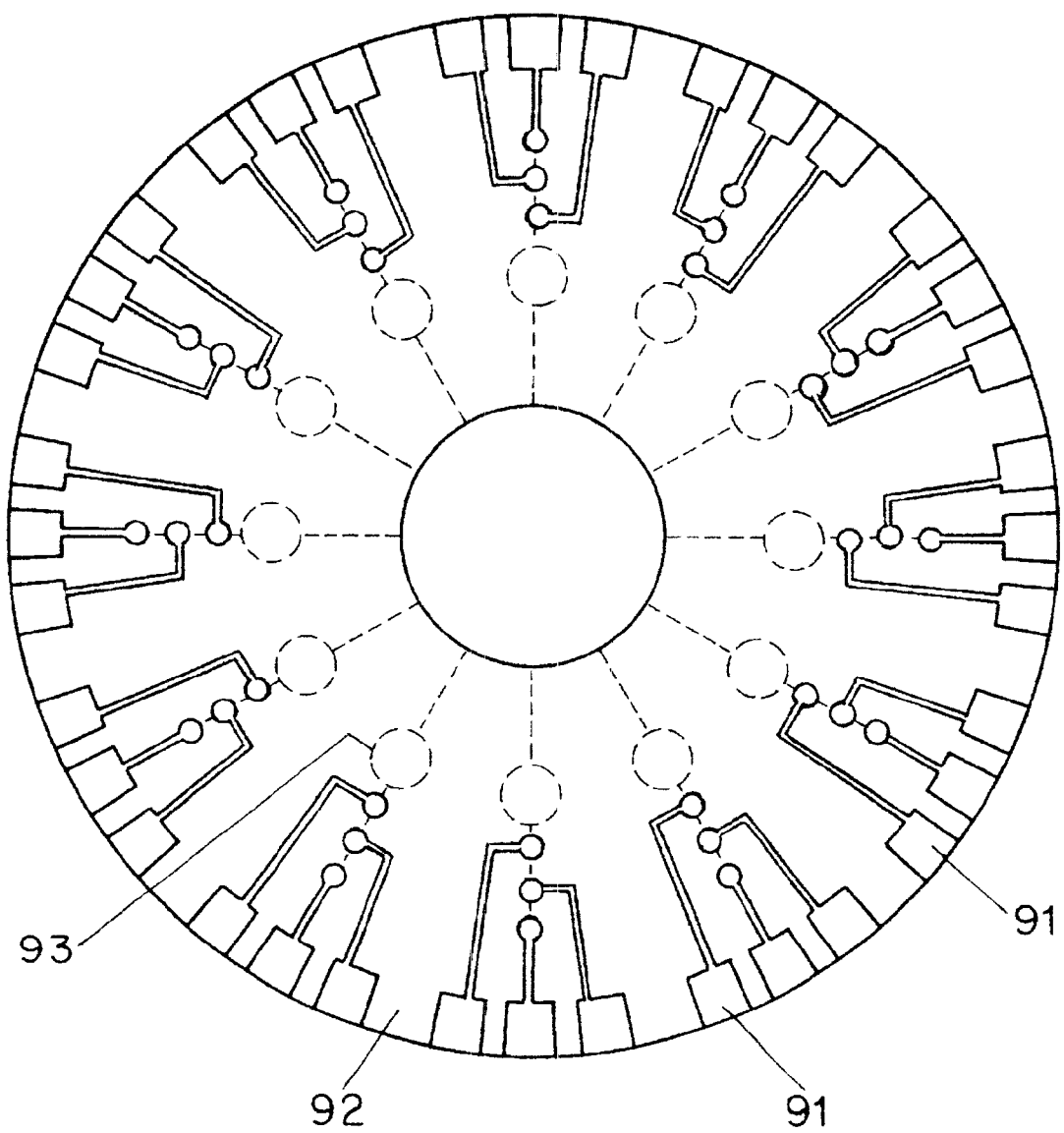
FIGS. 9A and B show the preparation of a sensor with multiple electrode sites.

The sensor disk 84 can be fabricated in much the same way as the sensor shown in FIGS. 5A–C. Thus, as illustrated in FIGS. 9A and B, contacts 91 are deposited around the periphery of a electrodes are deposited on substrate 92 in sets of three radially outwards from openings (or weak spots) 93. One of the electrodes in each set is a reference electrode, while the other two are working electrodes which include reagents appropriate for generating a signal indicative of the amount of the target analyte. Next, a mesh strip 94 is applied over each opening 93 and each set of electrodes. Over the top of the mesh an insulation layer 95 is formed. Once the sensor disk is formed, it is assembled with the other components to form the complete device.

Figure 9B:
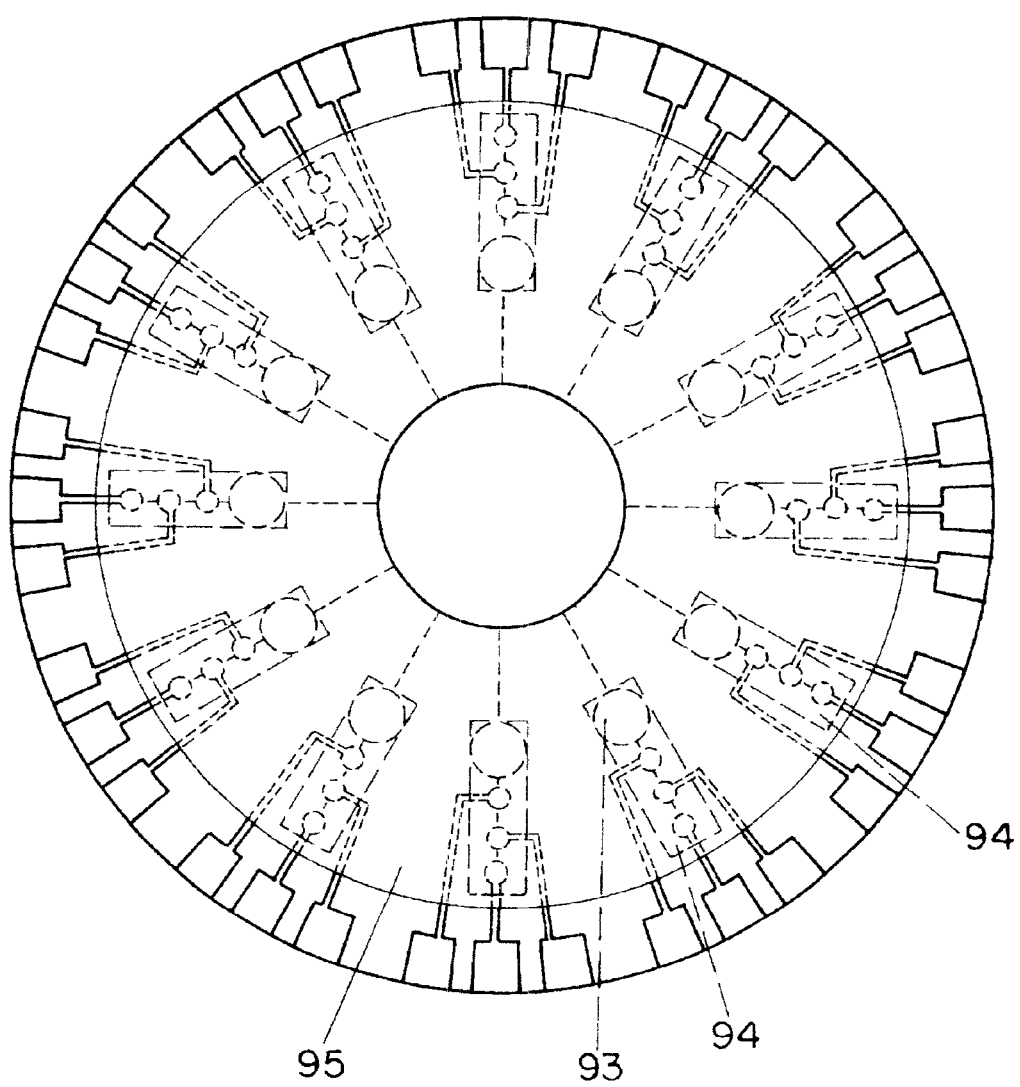
FIG. 9C shows an apparatus in accordance with the invention.
Figure 9C:
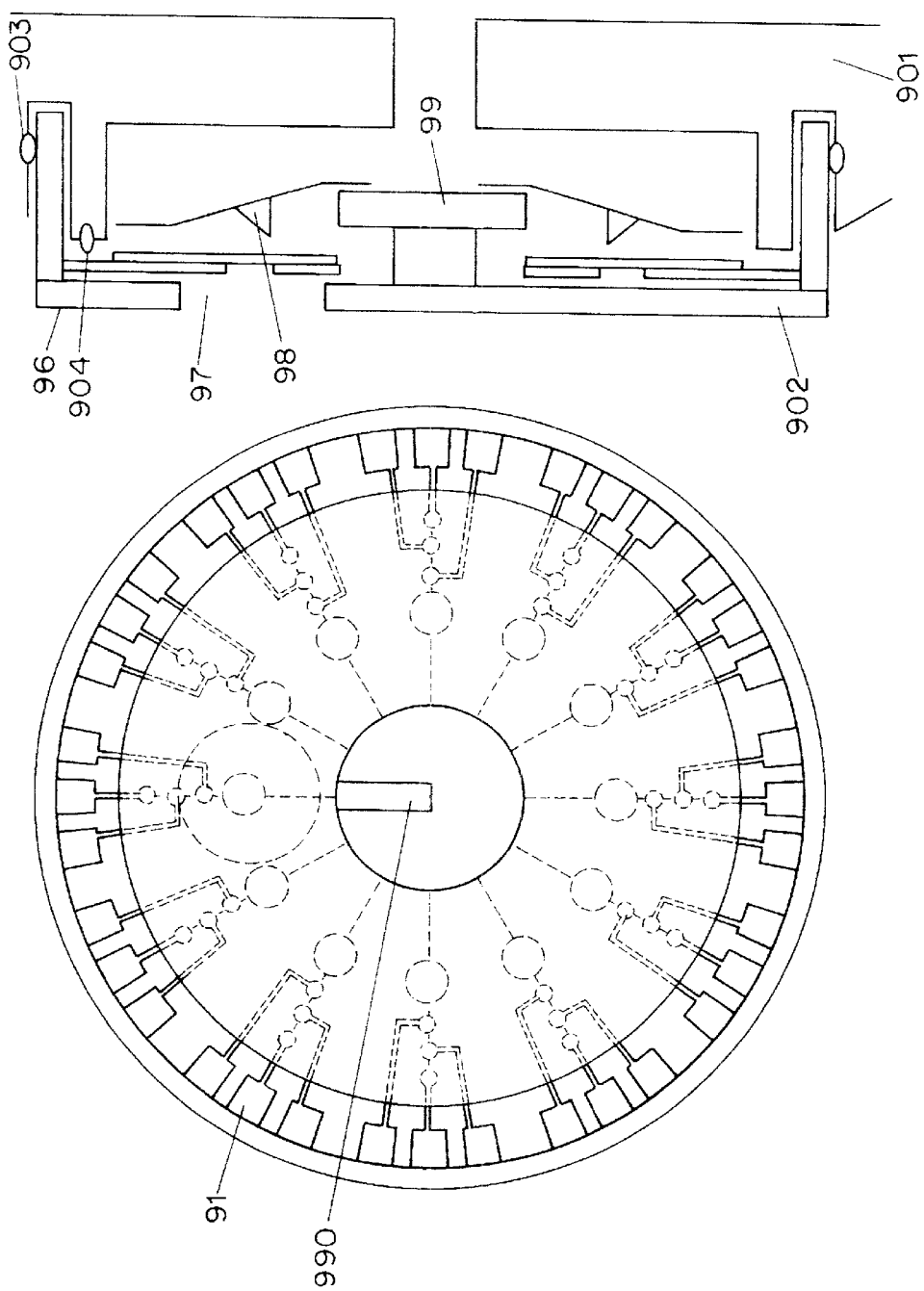

FIG. 9C provides a further view of such a device, which includes a skin contact ring 96 on the lower surface. The skin contact ring 96 surrounds an opening 97 through which the lancets 98 pass to pierce the skin of the user. This opening 96 moves with the rotation of the spindle 99, such that comes successively into alignment with each of the electrode sets. In the embodiment shown in FIG. 9C, the lancets are pre-tensioned by the spindle when the sensor assembly is put together. Slot 990 in the top of the spindle 99 allows the aligned lancet to drop through the spindle, to pierce the underlying skin. The upper case 901 of the assembly seals to the base portion 902 with an O-ring 903 seal. Electrical contact is made between this upper case 901 and contacts 91 via contact 904. This allow the analytical electronics to be located away from the sensor disk where they are not at risk of being exposed to fluid, and where they can be reused. Because of the sealing engagement of the upper case 901 with the base portion 902, the contact 904 also rotates and comes into contact with one electrode set at a time. In the case of a device "permanently" attached to the skin there would be as many skin-contact rings as there are sensors. Only the spindle moves, testing with a fresh lancet and a fresh sensor at a different sampling site each time.

Figure 10:
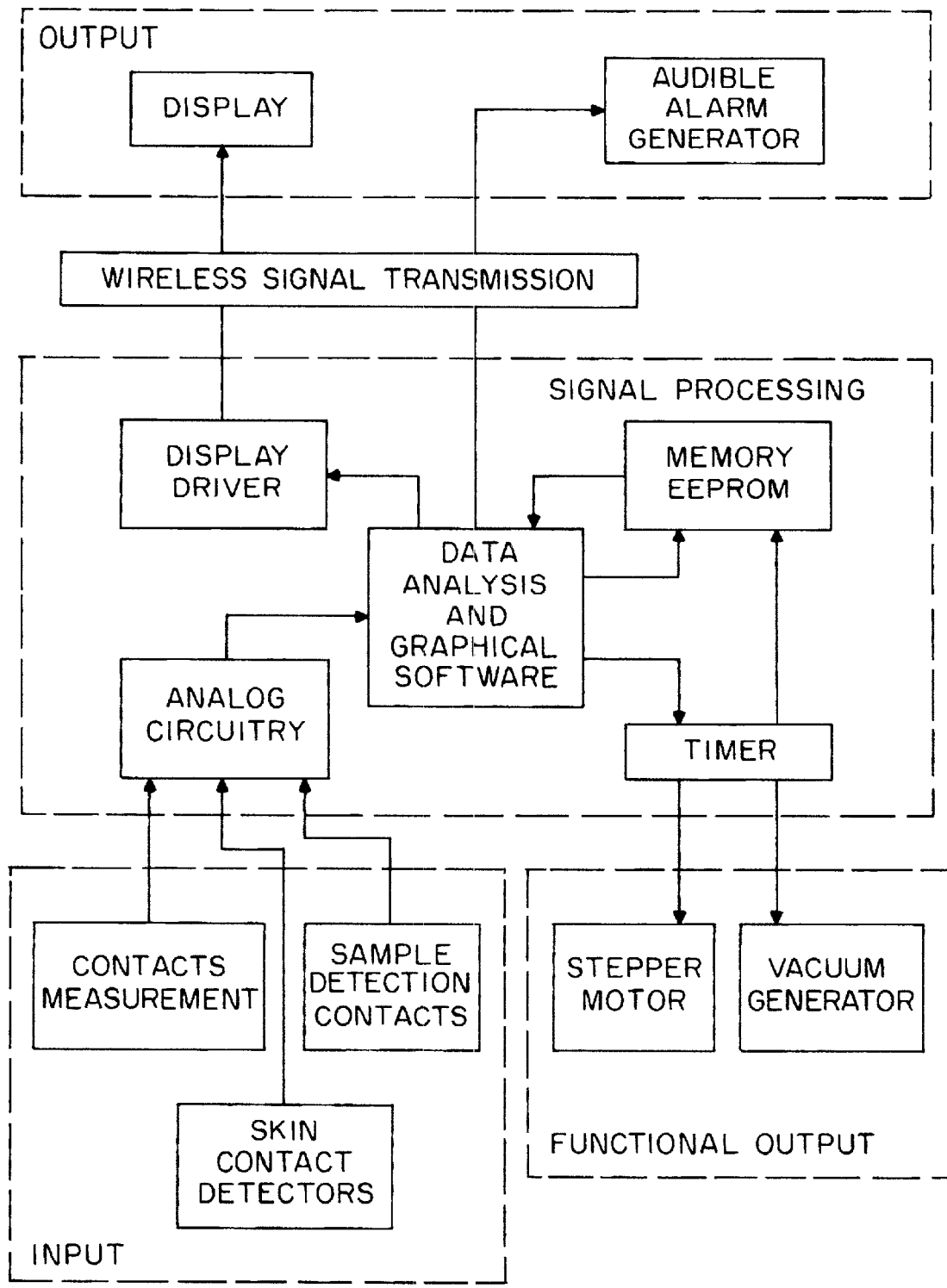
FIG. 10 shows a schematic representation of the electronics which can incorporated in an apparatus in accordance with the invention.

FIG. 10 shows a schematic representation of the electronics which can incorporated in a device in accordance with the invention. As shown, input signals are provided from the sensors and from any included skin-contact or sufficient-sample detector systems to a signal processing system. These signals are transmitted via analog circuitry to a processor which performs data analysis. This processor provides a signal to display driver which is connected (via a wired or wireless connection) to an output display. The processor may also provide a signal via a wired or wireless connection to an alarm generator. The display and the alarm generator together constitute the output portion of the device. The data analysis processor also communicates with a memory device, for example an EEPROM, in which information including calibration information and previous results may be stored. A timer is also provided which is activated by the data analysis software. This timer provides functional output signals to control a steeper motor (for rotating the sensor disk or spindle) and a vacuum generator (if present). Values from the timer may also be stored in the memory EEPROM for utilization by the data analysis processor.

The foregoing descriptions of various embodiments of the invention address show specific combinations of features. These descriptions and combinations should be viewed as merely exemplary, however, and do not exclude alternative implementations. For example, while the lancet ring 87 is shown with the free-ends of the lancets towards the center of the ring, it will be appreciated that an alternative geometry could be used in which the lancet ring has a star-like configuration in which the free-ends are pointed outwards. Similarly, the lancet ring could be pre-tensioned, in which case the cam ring would act to release rather than create tension. A further alternative is the use of a single actuating cam or hammer to activate the lancets. one-by-one, in turns, as they rotate through the position of the actuator.

The devices of the present invention may incorporate a variety of additional features which enhance the characteristics of the device and make it easier to use. For example, the devices may include an audible or otherwise detectable alarm which alerts the user that it is time to take a measurement. In the case of the device shown in FIG. 1, this alarm would indicate to the user that they need to insert a new lancet and sensor (if not already done) and take a measurement. In the case of a device such as that shown in FIG. 8 or 9, the alarm may actually precede the taking of a sample, so that the user will not be surprised by the lancet and will know to look at the display to observe the result.

The device, particularly the device of the type shown in FIG. 1, may also or additionally include an audible or otherwise detectable alarm which alerts the user that sufficient sample has been collected, and that the device can be removed. An audible alarm could take the form of a click, caused by the release of a detent within the device, or might be a beep generated electronically in the device. One way to achieve sufficient-sample indication is to assume that a pre-defined period of time is sufficient to collect the sample. In this case, the first appearance of a signal between one of the working electrodes and the reference, or between the separate sample-monitoring pair of electrodes starts a timer and the sufficient-sample indication is given some pre-defined period of time (for example 2 seconds) later. Sufficient sample may also be determined using an electrode pair having a spatial location and separation such that an electrical signal is only possible between the electrodes when sufficient sample is present. In either case, the signal which is collected can be any type of electronic signal, including signals based on conductivity, potential differences, or current flow (amperometric).

While the embodiment shown in FIG. 1 incorporates a skin-contact ring as a means to help with the expression of blood or fluid from the puncture, this skin-contact ring is optional, and can be replaced with other components such as a suction force generated by a mechanical or electrical pump for accomplishing the same function. A variable, user-selected vacuum force can be used to ensure sufficient bulging of the skin. A feedback mechanism tells the user that the skin made contact with the sensor. Two simple contacts bridged by the skin can achieve this. In an apparatus where the user is creating the vacuum (for example by drawing on a plunger), once the apparatus has detected the skin, the user is alerted, for example by an audible or visual signal that no more vacuum has to be created. In an automated apparatus, the pump mechanism can be shut down in response to this signal.

The device may include capacity for providing counseling to a user when abnormal readings are obtained for the analyte. Such counseling might be in the form of a prompt to call a physician, or might in appropriate cases instruct the user to administer medications. The audible signal can function as a hypoglycemic alarm, particularly in the multiple test embodiments. Such devices can also be used for overnight surveillance to alert the user or other concerned individual (for example a partner, parent or nurse) to changes in glucose levels.

The devices of the present invention offer a variety of advantages over existing devices for the measurement of glucose levels. To advantages flow directly from the incorporation of sampling and analysis functions in a single device. First, such devices require the user to perform fewer steps. Second, the user is not required to manipulate a small electrode into a slot in the meter. This allows for the utilization of smaller electrodes, which (as described in U.S. patent application Ser. No. 09/228,855, now U.S. Pat. No. 6,241,862, which is incorporated herein by reference) are both less expensive to make and more accurate in providing glucose measurements. Moreover, for embodiments in which there are a plurality of lancet/sensor pairs, the sampling site can be automatically varied throughout the course of a day, thus reducing injury resulting from repetitive punctures in the same location. The invention also allows the utilization of very small samples, which might otherwise be difficult to transfer to a sensor strip. This not only facilitates the taking of measurements with less pain, it can also provide for a more accurate result because of the benefits associated with small-sample measurements. In addition, the taking of a small sample which is optimally utilized by the device reduces or eliminates disposal issues for sample-contaminated waste.

What is claimed is:

1. An apparatus for detection and quantitation of an electrochemically-detectable analyte in blood or interstitial fluid, comprising:

a plurality of electrochemical sensors;

an equal plurality of cutting members wherein the plurality of electrochemical sensors are provided on a disk;

a meter unit comprising a housing, means disposed within the housing for engaging one of the cutting members and moving the engaged cutting member, a connector disposed within the housing for engaging one of the electrochemical sensors specific for the analyte and transmitting a signal from the sensor indicative of the amount of analyte, and a display operatively-associated with the connector for displaying the amount of the analyte to a user; wherein the cutting member is engaged within the housing; and the electrochemical sensor comprises an absorptive member for the uptake of a sample of blood or interstitial fluid, wherein the means for engaging and moving the cutting member moves the cutting member in a cycle from an initial position to a piercing position in which skin of the user is pierced, the electrochemical sensor being disposed such that the means for engaging and moving the cutting member causes the cutting member to pierce the sensor prior to piercing the skin of the user; the absorptive member taking up a sample from the pierced skin of the user when it is pierced by the lancet without movement of the apparatus.

2. The apparatus of claim 1, wherein the housing is a flattened disk having a top and a bottom surface, and further comprising a strap for holding the bottom surface of the housing against the skin of a user, wherein the electrochemical sensors are disposed adjacent to the bottom surface and the cutting members move to pierce the skin adjacent to the bottom surface.

3. The apparatus of claim 2, wherein the display is visible to the user when the bottom surface is held against the skin of the user.

4. The apparatus of claim 2, further comprising a timer operatively connected to the plurality of cutting members for automatically taking and evaluating a sample at predefined time intervals.

5. The apparatus of claim 4, wherein the time intervals are adjusted in response to amounts of analyte as determined by the apparatus.

6. The apparatus of claim 4, further comprising an alarm for indicating to the user that sufficient sample has been collected.

7. The apparatus of claim 6, further comprising an alarm for indicating to the user that it is time to take a sample.

8. The apparatus of claim 2, further comprising an alarm for indicating measured levels of analyte which are above or below preestablished thresholds.

9. The apparatus of claim 8, wherein the alarm transmits a signal to a remote receiver.

10. An apparatus for detection and quantitation of an electrochemically-detectable analyte in blood or interstitial fluid, comprising:

a plurality of electrochemical sensors;

a meter unit comprising a housing, means disposed within the housing for engaging a cutting member and moving the engaged cutting member, a connector disposed within the housing for engaging an electrochemical sensor specific for the analyte and transmitting a signal from the sensor indicative of the amount of analyte, and a display operatively-associated with the connector for displaying the amount of the analyte to user; wherein the cutting member is engaged within the housing;

the electrochemical sensor comprises an absorptive member for the uptake of a sample of blood or interstitial fluid, wherein the means for engaging and moving the cutting member moves the cutting member in a cycle from an initial position to a piercing position in which skin of the user is pierced, and wherein the electrochemical sensor is disposed such that the absorptive member takes up a sample from the pierced skin of the user when it is pierced by the lancet without movement of the apparatus;

the cutting member is a hollow cannula having a proximal end and a distal end, and wherein the proximal end is in juxtaposition with the electrochemical sensor to permit absorption of fluid passing through the hollow cannula by the absorptive member; and the plurality of electrochemical sensors are provided on a disk.

* * * * *